US011821028B2

(12) United States Patent
Wang (10) Patent No.: US 11,821,028 B2
(45) Date of Patent: Nov. 21, 2023

(54) SINGLE END DUPLEX DNA SEQUENCING

(71) Applicant: QIAGEN SCIENCES, LLC, Germantown, MD (US)

(72) Inventor: Yexun Wang, Ellicott City, MD (US)

(73) Assignee: QIAGEN Sciences, LLP, Germantown, MD (US)

( * ) Notice: Subject to any disclaimer, the term of this patent is extended or adjusted under 35 U.S.C. 154(b) by 403 days.

(21) Appl. No.: 16/316,832

(22) PCT Filed: Jul. 11, 2017

(86) PCT No.: PCT/US2017/041580
§ 371 (c)(1),
(2) Date: Jan. 10, 2019

(87) PCT Pub. No.: WO2018/013598
PCT Pub. Date: Jan. 18, 2018

(65) Prior Publication Data
US 2019/0241946 A1    Aug. 8, 2019

Related U.S. Application Data

(60) Provisional application No. 62/361,123, filed on Jul. 12, 2016.

(51) Int. Cl.
*C12Q 1/6869* (2018.01)
*C12Q 1/6806* (2018.01)
*C12Q 1/6855* (2018.01)
*C12Q 1/686* (2018.01)
*C12Q 1/6876* (2018.01)

(52) U.S. Cl.
CPC ......... *C12Q 1/6855* (2013.01); *C12Q 1/6806* (2013.01); *C12Q 1/686* (2013.01); *C12Q 1/6869* (2013.01); *C12Q 1/6876* (2013.01)

(58) Field of Classification Search
CPC ............................ C12Q 1/6806; C12Q 1/6855
See application file for complete search history.

(56) References Cited

U.S. PATENT DOCUMENTS

| | | | |
|---|---|---|---|
| 9,752,188 B2 | 9/2017 | Schmitt et al. | |
| 9,970,054 B2 | 5/2018 | Otwinowski et al. | |
| 10,011,871 B2 | 7/2018 | Bielas | |
| 2010/0222238 A1* | 9/2010 | Smith | C12N 15/1093 506/28 |
| 2012/0315635 A1* | 12/2012 | Vangbo | B01L 3/50273 435/6.11 |
| 2014/0100126 A1* | 4/2014 | Rabinowitz | G16B 20/00 506/9 |
| 2016/0032396 A1 | 2/2016 | Diehn et al. | |
| 2017/0211140 A1 | 7/2017 | Schmitt et al. | |
| 2017/0355984 A1 | 12/2017 | Evans et al. | |

FOREIGN PATENT DOCUMENTS

| | | |
|---|---|---|
| WO | 2008/093098 A2 | 8/2008 |
| WO | 2009/133466 A2 | 11/2009 |
| WO | 2015/100427 A1 | 7/2015 |
| WO | 2016/040901 A1 | 3/2016 |

OTHER PUBLICATIONS

Schmitt, Detection of ultra-rare mutations by next-generation sequencing, PNAS, 109:36, 14508-14513, 2012. (Year: 2012).*
Casbon et al., "A method for counting PCR template molecules with application to next-generation sequencing," *Nucleic Acids Research* 39(12):e81, 2011. (8 pages).
Fu et al., "Counting individual DNA molecules by the stochastic attachment of diverse labels," *PNAS* 108(22):9026-9031, 2011.
Jabara et al., "Accurate sampling and deep sequencing of the HIV-1 protease gene using a Primer ID," *PNAS* 108(50):20166-20171, 2011.
Kinde et al., "Detection and quantification of rare mutations with massively parallel sequencing," *PNAS* 108(23):9530-9535, 2011. (16 pages).
Kivioja et al., "Counting absolute numbers of molecules using unique molecular identifiers," *Nature Methods* 9(1):72-74, 2012. (5 pages).
Kozarewa et al., "Amplification-free Illumina sequencing-library preparation facilitates improved mapping and assembly of (G+C)-biased genomes," *Nature Methods* 6(4):291-295, 2009.
Patwardhan et al., "Massively parallel functional dissection of mammalian enhancers in vivo," *Nature Biotechnology* 30(3):265-270, 2012. (9 pages).
Schmitt et al., "Detection of ultra-rare mutations by next-generation sequencing," *PNAS* 109(36):14508-14513, 2012. (9 pages).
Shiroguchi et al., "Digital RNA sequencing minimizes sequence-dependent bias and amplification noise with optimized single-molecule barcodes," *PNAS* 109(4):1347-1352, 2012. (14 pages).
Zagordi et al., "Error correction of next-generation sequencing data and reliable estimation of HIV quasispecies," *Nucleic Acids Research* 38(21):7400-7409, 2010.

* cited by examiner

*Primary Examiner* — Angela M. Bertagna
*Assistant Examiner* — Carolyn L Greene
(74) *Attorney, Agent, or Firm* — Seed IP Law Group LLP (57) ABSTRACT

The present disclosure provides methods, sets of substantially complementary double-stranded adapters, and kits for performing nucleic acid sequencing. The substantial complementary double-stranded adapters comprise fully complementary molecular tag regions but one or more mismatches in other regions. Such adapters are ligated to double-stranded target nucleic acids, the obtained ligation products are amplified, and the generated amplification products are sequenced. The methods according to the present disclosure allow both strands of double-stranded target nucleic acids to be sequenced from one end of the target nucleic acids.

16 Claims, 5 Drawing Sheets
Specification includes a Sequence Listing.

1. DNA random fragmentation

2. Ligation

3. Amplification

SEQUENCE LISTING

```
<160> NUMBER OF SEQ ID NOS: 12

<210> SEQ ID NO 1
<211> LENGTH: 44
<212> TYPE: DNA
<213> ORGANISM: Artificial Sequence
<220> FEATURE:
<223> OTHER INFORMATION: Synthetic complementary double-stranded adapter
      sequence
<220> FEATURE:
<221> NAME/KEY: misc_feature
<222> LOCATION: (1)...(44)
<223> OTHER INFORMATION: n = A,T,C or G

<400> SEQUENCE: 1
acactctttc cctacacgct cttccgatcn nnnnnnnnng tcat                    44

<210> SEQ ID NO 2
<211> LENGTH: 46
<212> TYPE: DNA
<213> ORGANISM: Artificial Sequence
<220> FEATURE:
<223> OTHER INFORMATION: Synthetic complementary double-stranded adapter
      sequence
<220> FEATURE:
<221> NAME/KEY: misc_feature
<222> LOCATION: (1)...(46)
<223> OTHER INFORMATION: n = A,T,C or G

<400> SEQUENCE: 2
tgacnnnnnn nnnngatcgg aagagctgag tgtagggaaa gagtgt                  46

<210> SEQ ID NO 3
<211> LENGTH: 91
<212> TYPE: DNA
<213> ORGANISM: Artificial Sequence
<220> FEATURE:
<223> OTHER INFORMATION: Synthetic complementary double-stranded adapter
      sequence
<220> FEATURE:
<221> NAME/KEY: misc_feature
<222> LOCATION: (1)...(91)
<223> OTHER INFORMATION: n = A,T,C or G
```

<400> SEQUENCE: 3
aatgatacgg cgaccaccga gatctacact ctttccctac acgacgctct tccgatctnn    60
nnnnnnnntt cttagcgatt attggagtcc t                                    91

<210> SEQ ID NO 4
<211> LENGTH: 90
<212> TYPE: DNA
<213> ORGANISM: Artificial Sequence
<220> FEATURE:
<223> OTHER INFORMATION: Synthetic complementary double-stranded adapter
      sequence
<220> FEATURE:
<221> NAME/KEY: misc_feature
<222> LOCATION: (1)...(90)
<223> OTHER INFORMATION: n = A,T,C or G

<400> SEQUENCE: 4
ggactccaat ggtcgctaag aannnnnnnn nnagatcgga agagcgtcgt gtagggaaag    60
agtgtagatc tcggtggtcg ccgtatcatt                                      90

<210> SEQ ID NO 5
<211> LENGTH: 93
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (1)...(93)
<223> OTHER INFORMATION: n = A,T,C or G

<400> SEQUENCE: 5
aatgatacgg cgaccaccga gatctacact ctttccctac acgacgctct tccgatctnn    60
nnnnnnnnnn ttctgagcga ttataggagt cct                                  93

<210> SEQ ID NO 6
<211> LENGTH: 22
<212> TYPE: DNA
<213> ORGANISM: Artificial Sequence
<220> FEATURE:
<223> OTHER INFORMATION: Primer sequence
<220> FEATURE:
<221> NAME/KEY: modified_base
<222> LOCATION: 1
<223> OTHER INFORMATION: Phosphorus

<400> SEQUENCE: 6 ggactccctat ggtcgctcag aa                                             22

<210> SEQ ID NO 7
<211> LENGTH: 21
<212> TYPE: DNA
<213> ORGANISM: Artificial Sequence
<220> FEATURE:
<223> OTHER INFORMATION: Primer sequence

<400> SEQUENCE: 7
aatgtacagt attgcgtttt g                                               21

<210> SEQ ID NO 8
<211> LENGTH: 20
<212> TYPE: DNA
<213> ORGANISM: Artificial Sequence
<220> FEATURE:
<223> OTHER INFORMATION: Illumina F primer sequence

```
<400> SEQUENCE: 8
aatgatacgg cgaccaccga                                               20

<210> SEQ ID NO 9
<211> LENGTH: 58
<212> TYPE: DNA
<213> ORGANISM: Artificial Sequence
<220> FEATURE:
<223> OTHER INFORMATION: Universal primer (IL2)

<400> SEQUENCE: 9
aatgatacgg cgaccaccga gatctacact ctttccctac acgacgctct tccgatct     58

<210> SEQ ID NO 10
<211> LENGTH: 79
<212> TYPE: DNA
<213> ORGANISM: Artificial Sequence
<220> FEATURE:
<223> OTHER INFORMATION: IL1 ID(#)-RS2 primer

<400> SEQUENCE: 10
caagcagaag acggcatacg agatgtgact ggagttcaga cgtgtgctct tccgatctaa   60
tgtacagtat tgcgttttg                                                79

<210> SEQ ID NO 11
<211> LENGTH: 29
<212> TYPE: DNA
<213> ORGANISM: Artificial Sequence
<220> FEATURE:
<223> OTHER INFORMATION: Primer sequence

<400> SEQUENCE: 11
acactctttc cctacacgct cttccgatc                                     29

<210> SEQ ID NO 12
<211> LENGTH: 22
<212> TYPE: DNA
<213> ORGANISM: qArtificial Sequence
<220> FEATURE:
<223> OTHER INFORMATION: Primer sequence

<400> SEQUENCE: 12
ggactccaat ggtcgctaag aa                                            22
```

SINGLE END DUPLEX DNA SEQUENCING

CROSS REFERENCE TO RELATED APPLICATION

This application claims the benefit under 35 U.S.C. § 119(e) to U.S. Provisional Application No. 62/361,123, filed Jul. 12, 2016, which application is hereby incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 830109_413USPC_SEQUENCE_LISTING. The text file is 3,432 bytes, was created on Dec. 11, 2018, and is being submitted electronically via EFS-Web.

BACKGROUND

Technical Field

The present disclosure relates to methods, adapters and kits for performing single end duplex DNA sequencing.

Description of the Related Art

Next-generation sequencing technology has been used in DNA sequencing for mutation detection and in RNA-Sequencing for transcriptome profiling. However, the error rate associated with this technology in current sequencing platforms prevents it from confident identification of rare mutations.

Previous studies have assigned each original DNA template with a unique barcode to correct the amplification bias and sequencing error. Among different approaches using molecular barcodes, duplex sequencing has shown the best ability to correct for DNA base errors generated during sample preparation, thus best accuracy in detecting very low fraction of mutations. Duplex sequencing takes advantage of complementary nature of two strands of DNA and confirms only variants that are present in both strands of DNA. Because the probability of two errors happening at the same exact base pair in both strands and resulting in a complementary base pair is very low, duplex sequencing increases the accuracy of sequencing significantly. However, duplex sequencing currently relies on pair-end sequencing.

SUMMARY

The present disclosure provides methods, adapters and kits for performing single end duplex DNA sequencing.

In one aspect, the present disclosure provides a method for performing DNA sequencing, comprising:
(a) performing a ligation reaction in the presence of a plurality of double-stranded target nucleic acids and a first set of substantially complementary double-stranded adapters to generate ligation products,
wherein each adapter of the first set comprises a first strand and a second strand,
the first strand comprises, from 5' to 3', a 5' region that is 10 or more nucleotides in length, a molecular tag sequence, and an optional 3' region,
the second strand comprises, from 3' to 5', a 3' region that comprises a sequence fully complementary to a 10-nucleotide or longer portion of the 5' region of the first strand, a fully complementary sequence of the molecular tag sequence of the first strand, and an optional 5' region,
at least one mismatch between the first and second strands is located in the 3' region of the first strand if the 3' region is present, and/or in the 5' region that is 3' to the 10-nucleotide or longer portion of the 5' region of the first strand, and
different adapters of the first set comprise different molecular tag sequences in their first strands and corresponding fully complementary sequences of the different molecular tag sequences in their second strands, but are otherwise identical to each other,
(b) performing an amplification reaction using the ligation products of step (a) as templates to generate amplification products, wherein the amplification products comprise one or more locations that do not form complementary base pairs in the first and second strands of the substantially complementary double-stranded adapters, and
(c) performing sequencing reactions using amplification products of step (b) or their further amplification products as templates to obtain sequence reads that comprise the one or more locations where a complementary base pair is not formed in the first and second strands of the double-stranded adapters.

In another aspect, the present application provides a set of substantially complementary double-stranded adapters, comprising at least 16 different adapters, wherein
each adapter of the set comprises a first strand and a second strand,
the first strand comprises, from 5' to 3', a 5' region, a molecular tag sequence, and an optional 3' region,
the second strand comprises, from 3' to 5', a 3' region that comprises a sequence fully complementary to a 10-nucleotide or longer portion of the 5' region of the first strand, a fully complementary sequence of the molecular tag sequence of the first strand, and an optional 5' region,
at least one mismatch between the first and second strands is located in the 3' region of the first strand if the 3' region is present, and/or in the 5' region that is 3' to the 10-nucleotide or longer portion of the 5' region of the first strand, and
different adapters comprise different molecular tag sequences in their first strands and corresponding fully complementary sequences of the different molecular tag sequences in their second strands, but are otherwise identical to each other.

In another aspect, the present disclosure provides a kit, comprising:
(1) a set of substantially complementary double-stranded adapters provided herein, and
(2) a ligase.

DETAILED DESCRIPTION

Although next-generation sequencing technology has been widely used in DNA mutation detection, various errors can be introduced during sample preparation and sequencing process for DNA mutation detection with next-generation sequencing. These error prone processes include sequence-dependent bias and amplification noise from reverse transcription, adapter ligation, library amplification by PCR, solid-phase clonal amplification and sequencing, and polymerase errors generating point mutations during amplification and sequencing.

A number of improvements have been developed to reduce sequencing related bias and errors at the level of biochemistry and data analysis. Recently, exogenous tagging of sequencing fragment before amplification has been reported to reduce bias and sequencing errors. Because all amplicons derived from a particular starting molecule can be explicitly identified, any variation in the sequence or copy number of identically tagged sequencing reads can be considered as technical errors.

Nevertheless, because prevailing next-generation sequencing platforms generate sequence data from single-stranded fragments of DNA, artifactual mutations introduced during the initial round of PCR amplification are undetectable as errors—even with molecular barcodes. More importantly, spontaneous DNA damage arising from normal metabolic processes and additional DNA damage generated ex vivo during tissue processing and DNA extraction (e.g., in FFPE DNA) cannot be detected with molecular barcodes.

One solution to the above problem is to use duplex sequencing (i.e., sequencing performed using both strands of a target DNA as templates). Because DNA naturally exists as a double-stranded entity with one strand reciprocally encoding the sequence information of the other strand, it is feasible to identify and correct nearly all forms of sequencing errors by comparing the sequence of individual tagged amplicons derived from one strand of a double-stranded complex with those of the other strand of the same molecule. Because the two strands are complementary, true mutations are found at the same position in both strands.

One limitation of using molecular barcodes in duplex sequencing is that pair-end sequencing is required. Pair-end sequencing in turn requires molecular barcodes at both ends, preparation of which is more complex and time consuming than single-end sequencing, which requires attaching molecular barcodes at only one end of target nucleic acids. In addition, certain sequencers (e.g., the ION PROTON™ system) can be used only for performing single end sequencing, not pair-end sequencing.

At present, sequencing one end of a molecular barcoded sequencing library cannot reconstruct the relationship of two complementary strands from the same double-stranded target nucleic acid.

The present disclosure overcomes the above limitation by providing methods for performing single end duplex DNA sequencing (i.e., sequencing both strands of a double-stranded target DNA molecule from one end of the target DNA molecule). Such methods are able to establish the relationship of two complementary strands from the same double-stranded target DNA molecule with a molecular tag on only one side of the molecule, thus enabling implementing duplex sequencing using single end sequencing.

This molecular tagging system can also be combined with single primer enrichment for targeted DNA sequencing with ultrahigh accuracy. Single primer enrichment allows for more design flexibility than targeted enrichments using two primers, and capture of certain unknown sequence information (e.g., sequence deletion or translocation) that would be not possible when two primers are used for targeted enrichments.

In the following description, any ranges provided herein include all the values in the ranges. It should also be noted that the term "or" is generally employed in its sense including "and/or" (i.e., to mean either one, both, or any combination thereof of the alternatives) unless the content dictates otherwise. Also, as used in this specification and the appended claims, the singular forms "a," "an," and "the" include plural referents unless the content dictates otherwise. The terms "include," "have," "comprise" and their variants are used synonymously and to be construed as non-limiting. The term "about" refers to ±10% of a reference a value. For example, "about 50° C." refers to "50° C.±5° C." (i.e., 50° C.±10% of 50° C.).

Methods of Single End Duplex DNA Sequencing

In one aspect, the present disclosure provides a method for performing DNA sequencing, comprising:

(a) performing a ligation reaction in the presence of a plurality of double-stranded target nucleic acids and a first set of substantially complementary double-stranded adapters to generate ligation products,
wherein each adapter of the first set comprises a first strand and a second strand,
the first strand comprises, from 5' to 3', a 5' region that is 10 or more nucleotides in length, a molecular tag sequence, and an optional 3' region,
the second strand comprises, from 3' to 5', a 3' region that comprises a sequence fully complementary to a 10-nucleotide or longer portion of the 5' region of the first strand, a fully complementary sequence of the molecular tag sequence of the first strand, and an optional 5' region,
at least one mismatch between the first and second strands is located in the 3' region of the first strand if the 3' region is present, and/or in the 5' region that is 3' to the 10-nucleotide or longer portion of the 5' region of the first strand, and
different adapters of the first set comprise different molecular tag sequences in their first strands and corresponding fully complementary sequences of the different molecular tag sequences in their second strands, but are otherwise identical to each other, (b) performing an amplification reaction using the ligation products of step (a) as templates to generate amplification products, wherein the amplification products comprise one or more locations that do not form complementary base pairs in the first and second strands of the substantially complementary double-stranded adapters, and (c) performing sequencing reactions using amplification products of step (b) or their further amplification products as templates to obtain sequence reads that comprise the one or more locations where a complementary base pair is not formed in the first and second strands of the double-stranded adapters.

1. Ligation

Step (a) of the method provided herein is to perform a ligation reaction to ligate target nucleic acids with adapters to obtain adapter-linked target nucleic acids.

a. Adapters i. First Set of Adapters

The ligation is performed in the presence of a first set of substantially complementary double-stranded adapters.

As used herein, the terms "double-stranded adapter" and "double-stranded adaptor" refer to a double-stranded DNA molecule that can be ligated to another nucleic acid molecule (e.g., a target nucleic acid molecule). Preferably, each strand of an adapter is not substantially complementary to target nucleic acids in a sample.

Each adapter of the first set comprises a first strand and a second strand wherein the first strand is substantially complementary to the second strand.

The terms "complementary" and "complement" and their variants, as used herein, refer to any two nucleotide sequences that form a hybridized duplex by base pairing.

One nucleotide sequence may be "completely complementary" or "fully complementary" to another nucleotide sequence if all of the nucleotides in the sequence form base pairing with nucleotides in the corresponding antiparallel positions of the other sequence.

"Partial" complementarity describes nucleotide sequences in which at least 50%, but less than 100%, of the nucleotides of one sequence form base pairing with nucleotides in the corresponding antiparallel positions of the other sequence.

One nucleotide sequence is "substantially complementary" to another nucleotide sequence if the two sequences are sufficiently but not completely complementary to each other so that they are able to form a double-stranded like structure (i.e., the two sequences anneal to each other) under appropriate annealing conditions (e.g., heating a mixture comprising the two nucleotide sequences to a high temperature such as about 95° C. and gradually cooling down to a lower temperature such as about 25° C.). In certain embodiments, one nucleotide sequence substantially complementary to another nucleotide sequence has at least 80% (e.g., at least 85%, at least 90%, at least 95%, at least 98%, or at least 99%) nucleotides complementary to nucleotides in the corresponding antiparallel positions of the other sequence.

The first strand comprises, from 5' to 3', a 5' region, a molecular tag sequence, and an optional 3' region. The 5' region is at least 10 nucleotides long, and may be from 10 to 100 nucleotides long, such as from 15 to 75 nucleotides long. The molecular tag sequence may be 2 to 15 nucleotides long, such as 3, 4, 5, 6, 7, 8, 9, 10, 11, 12, 13, or 14 nucleotides long.

The molecular tag (also referred to as "molecular barcode" or "barcode") sequence of the first strand may be a completely defined sequence. Alternatively, it may be a random or semi-random sequence.

A "defined" or "completely defined" sequence is a sequence that has a specific nucleotide (i.e., A, T, G, or C) at each position of the sequence.

A "random sequence" or "completely random sequence" refers to a nucleotide sequence where any one of the four nucleotides (i.e., A, T, G, and C) may be present at any position in the nucleotide sequence. For example, a random hexamer has a sequence of NNNNNN where "N" may be any of A, T, G, and C.

A "semi-random sequence" refers to a sequence other than a completely defined sequence or a completely random sequence. It includes a nucleotide sequence where (1) in at least one position ("semi-random position"), any one of two or three different nucleotides may be present, or (2) in at least one position ("random position"), any one of the four nucleotides (i.e., A, T, G, and C) may be present and in at least another position, a defined nucleotide is present. For example, the sequence DDDDDD where "D" may be any of A, T and G is a semi-random sequence, which comprises 6 semi-random positions (i.e., where "D" is located). The sequence NNANNA where "N" may be any of A, T, G, and C is also a semi-random sequence, which comprises 4 random positions (i.e., where "N" is located) and 2 positions with a defined nucleotide (i.e., A). The sequence NNDNND is another type of semi-random sequences that consist of both semi-random positions and random positions. The sequence NDANDA is yet another type of semi-random sequences that comprise semi-random positions, random positions, and one or more positions with defined nucleotide(s).

The first strand of the adapter may or may not comprise a 3' region. If the 3' region is present in the first strand, it may be 2 to 30 nucleotides long, such as 4 to 20 or 5 to 15 nucleotides long.

The second strand comprises, from 3' to 5', a 3' region that comprises a sequence fully complementary to a 10-nucleotide or longer portion of the 5' region of the first strand, a fully complementary sequence of the molecular tag sequence of the first strand, and an optional 5' region, at least one mismatch between the first and second strands is located in (a) the 3' region of the first strand if the 3' region is present, (b) the 5' region of the first strand that is 3' to the 10-nucleotide or longer portion of the 5' region of the first strand, or both (a) and (b). Preferably, the mismatches are located in (a) or (b), not both (a) and (b).

The substantially complementary double-stranded adapter may be formed by annealing the first strand and the second strand to each other. The resulting adapter thus contains at least two regions where the first strand is completely complementary to the second strand: The first region is formed between a 10-nucleotide or longer portion of the 5' region of the first strand and its complementary sequence in the 3' region of the second strand, and the second region is formed between the molecular tag sequence of the first strand and its completely complementary sequence in the second strand.

The first completely complementary region of the adapter allows the design of an amplification primer for amplifying the ligation products and subsequent single-end sequencing of the amplified products. Because in the ligation products, the mismatch(es) of the adapter is located 3' to the first completely complementary region in the first strand of the adapter, the amplification products contain mismatched nucleotide(s) useful for distinguishing the two strands of a target nucleic acid ligated to the adapter. The second completely complementary region of the adapter, one the other hand, allows the association of the two strands originated from the same target nucleic acid. The presence of both the first and second completely complementary regions in the adapter thus allows obtaining sequence information of both strands of a target nucleic acid by single end sequencing (i.e., performing sequencing form one end of the target nucleic acid).

The substantially complementary double-stranded adapter contains at least one mismatch between its first and second strands. In certain embodiments, it contains 2, 3, 4, 5, or 6 mismatches.

A mismatch occurs when a nucleotide in the first or second strand of a substantially complementary double-stranded adapter does not form a complementary base pair with a nucleotide in the other strand. A mismatch may be a nucleotide insertion, a nucleotide deletion, or a nucleotide substitution.

The first strand and the second strand of the adapter may or may not have the same length. Preferably, there is an extra "T" at the 3' terminus of the first strand of the adapter to facilitate ligation with target nucleic acids having an A overhang.

The first strand of the adapter may be 12 to 120 nucleotides long, such as 20 to 110 or 30 to 100 nucleotides long. Similarly, the second strand of the adapter may be 12 to 120 nucleotides long, such as 20 to 110 or 30 to 100 nucleotides long.

Figure 1A:
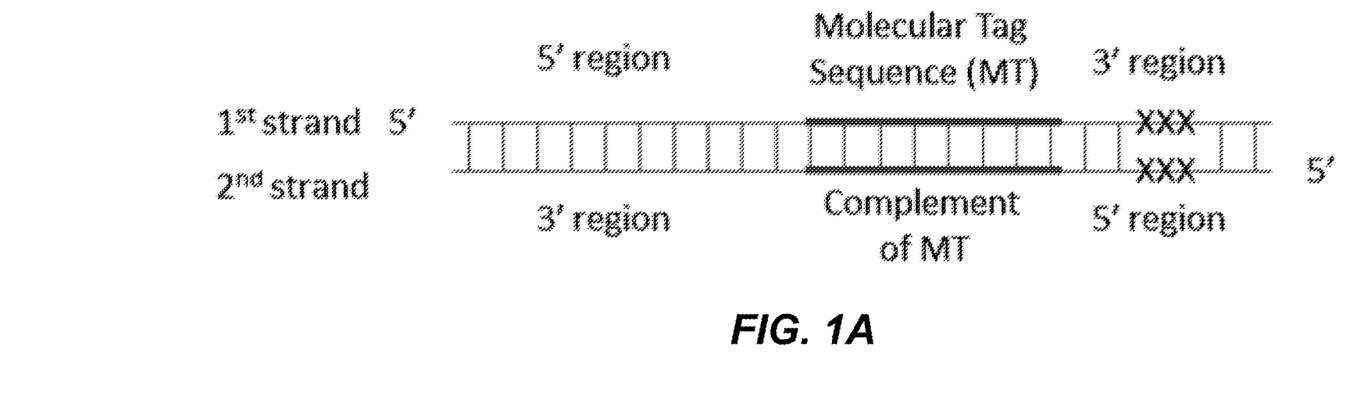
FIGS. 1A to 1D are schematic representations of exemplary substantially complementary double-stranded adapters.

An exemplary substantially complementary double-stranded adapter is shown in FIG. 1A. The first stand of the adapter comprises, from 5' to 3', a 5' region, a molecular tag (MT) sequence, and a 3' region. The second strand of the adapter comprises, from 3' to 5', a 3' region, a fully complementary sequence of the molecular tag sequence (complement of MT) and a 5' region. The first and second strands are completely complementary to each other except at 3 nucleotide positions (indicated with "X") in the 3' region of the first strand and the 5' region of the second strand.

Figure 1B:
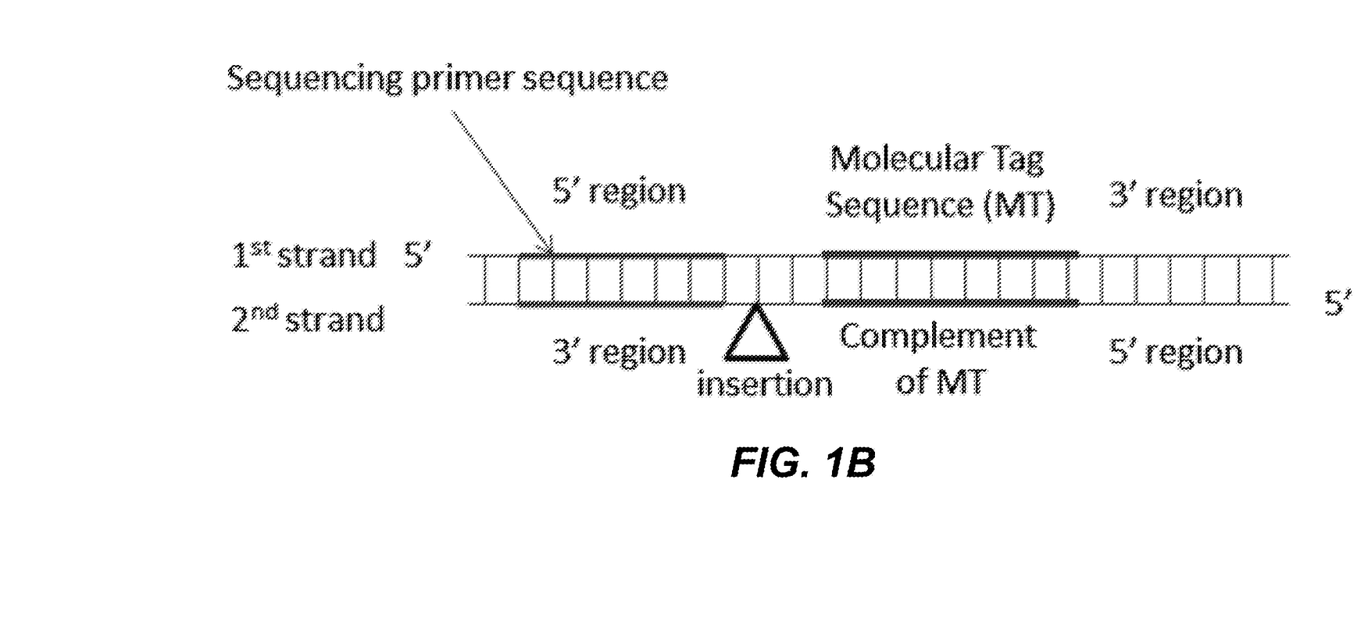

In certain embodiment, the 5' region of the first strand of the adapter comprises a sequencing primer sequence, and the 3' region of the second strand of the adapter comprises the completely complimentary sequence of the sequencing primer sequence. An exemplary adapter is shown in FIG. 1B. The first and second strands of the adapter are completely complementary to each other except that in the second strand, an insertion is located 5' to the sequence complementary to the sequencing prime sequence.

Figure 1C:
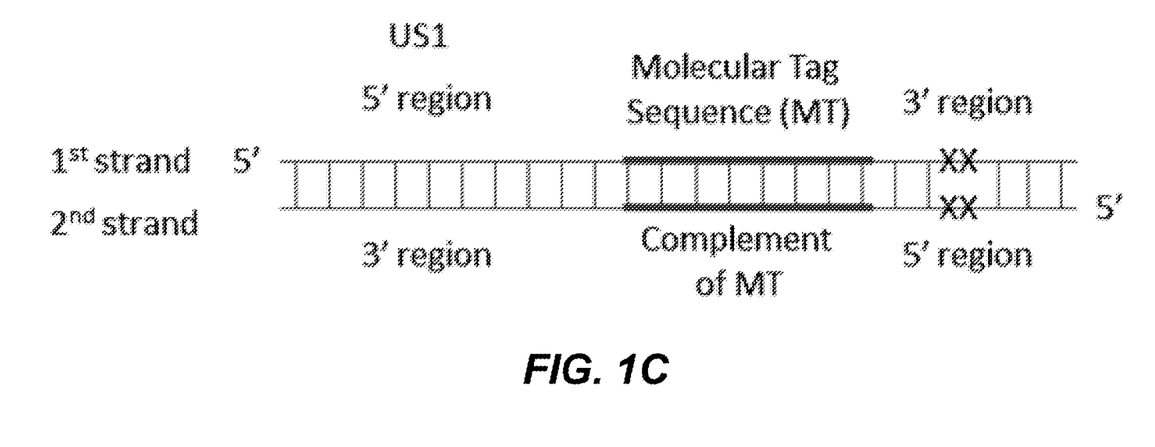

FIG. 1C shows another exemplary substantially complementary double-stranded adapter. In this adapter, the first and second strands are completely complementary to each other except that in two nucleotide mismatches (indicated by "X") in the 3' region of the first strand and the 5' region of the second strand. The 5' region of the first strand comprises a first universal primer sequence (US1), which may be used for designing a PCR primer for amplifying adapter-linked target nucleic acids. Preferably, this sequence does not have significant homology (i.e., US1 has less than 50% sequence identity over its full length) to target nucleic acids of interest or other nucleic acids in a nucleic acid sample. The US1 sequence may be from 11 to 35 nucleotides in length, such as from 15 to 25 nucleotides in length.

Figure 1D:
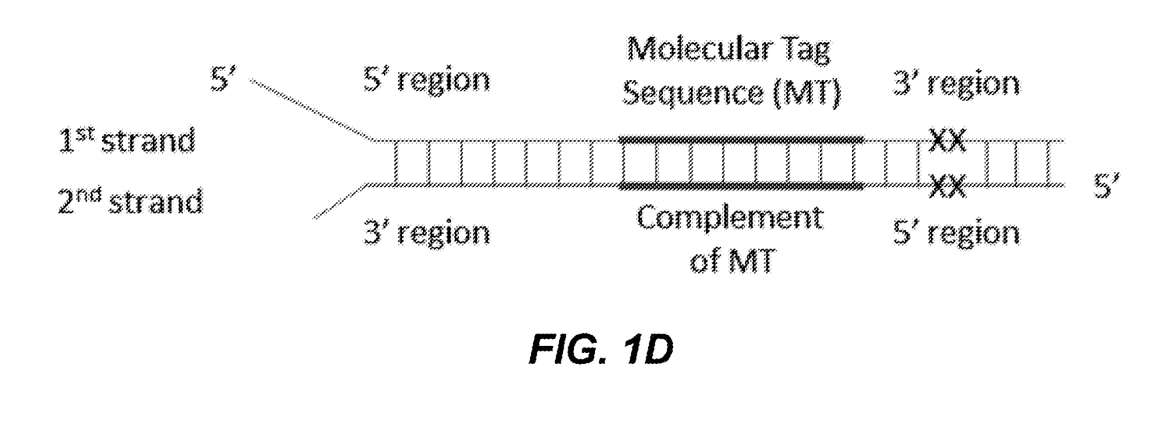

A further exemplary substantially complementary double-stranded adapter is showt in FIG. 1D. In addition to two mismatches (indicated by "X") in the 3' region of the first stand and the 5' region of the second strand, a portion at the 5' terminus of the first strand is not substantially complementary to a portion at the 3' terminus of the second strand. The remaining portion (which is 10 or more nucleotides long) of the 5' region of the first strand is completely complementary to the remaining portion of the 3' region of the second strand.

A specific substantially complementary double-stranded adapter is shown below (SEQ ID NOS: 1 and 2):

5' ACACTCTTTCCCTACAC GCTCTTCCGATCNNNNNNNNNNGTCAT

3' TGTGAGAAAGGGATGTGAGTCGAGAAGGCTAGNNNNNNNNNNCAGT

In the above adapter, the first strand (i.e., the upper strand) contains a 10-nucleotide random molecular tag sequence (i.e., NNNNNNNNNN). In the 3' region of the second strand (i.e., the lower strand), there is a 3-nucleotide insertion (i.e., AGT). There is an extra "T" at the 3' terminus of the first strand.

Another specific substantially complementary double-stranded adapter is shown below (SEQ ID NOS: 3 and 4):

5'AATGATACGGCGACCACCGAGATCTACACTCTTTCCCTACACGACGCT

CTTCCGATCTNNNNNNNNNNTTCTTAGCGATTATTGGAGTCCT 3'

3'TTACTATGCCGCTGGTGGCTCTAGATGTGAGAAAGGGATGTGCTGCGA

GAAGGCTAGANNNNNNNNNNAAGAATCGCTGGTAACCTCAGG 5'

In the above adapter, the first strand (i.e., the upper strand) contains a 10-nucleotide random molecular tag sequence (i.e., NNNNNNNNNN). In the 3' region of the first strand and the 5' region of the second strand (i.e., the lower strand), there are two mismatches (i.e., "TT" in the first strand and "GG" in the second strand). There is also an extra "T" at the 3' terminus of the first strand. The underlined sequence is the sequence of Illumina sequencing primer.

As indicated above, step (a) of the method disclosed herein uses a first set of different adapters, each of which is described above. Different adapters of the first set comprise different molecular tag sequences in their first strands and corresponding fully complementary sequences of the different molecular tag sequences in their second strands, but are otherwise identical to each other.

For adapters that comprise defined molecular tag sequences, a set of such adapters may be prepared by first synthesizing each adapter separately and then pooling them together. For each adapter, the first strand and the second strand may be synthesized separately to generate the first stand comprising a defined molecular tag sequence and the second strand comprising the completely complementary sequence of the defined molecular tag sequence. After both strands are synthesized, they may be annealed together in a solution under controlled heating and cooling. Once all different adapters are combined together, they may be used in a ligation reaction to ligate target nucleic acid.

Figure 2:
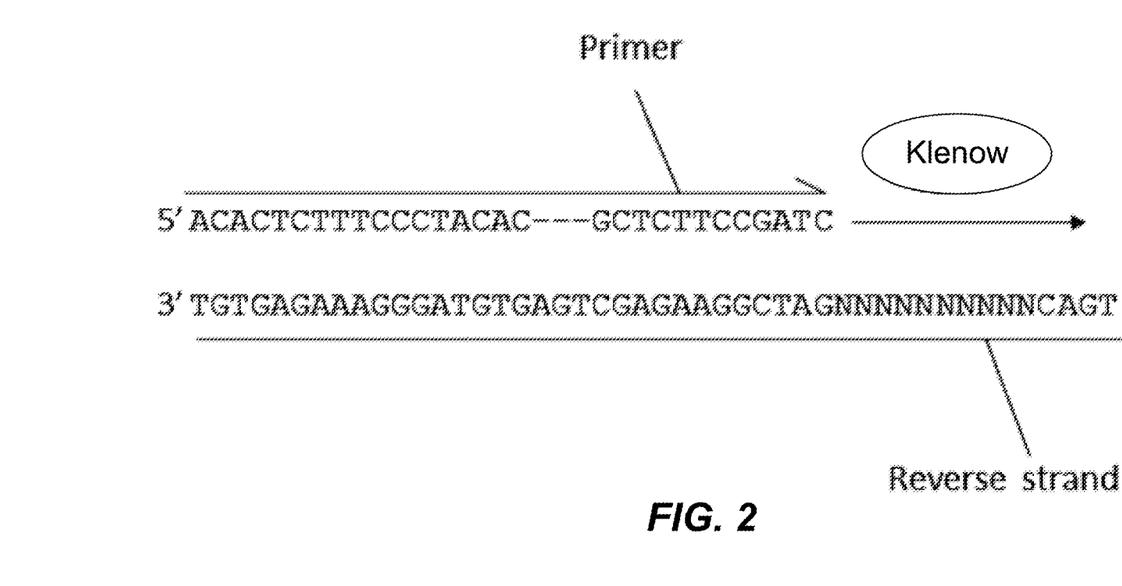
FIG. 2 is a schematic representation of preparing an exemplary substantially complementary double-stranded adapter (SEQ ID NOS: 11 and 2 respectively).

For adapters that comprise random or semi-random molecular tag sequences, a set of such adapters may be prepared by randomly or semi-randomly synthesizing the complement of a molecular tag region in the second strand, and then using this second strand as a template to form a double-stranded adapter via primer extension. An illustration of this process is shown in FIG. 2. The reverse strand (i.e., the second strand of the adapter) is first synthesized to contain the complement of a molecular tag region (i.e., NNNNNNNNNN). A primer that is completely complementary to the 3' region of the second strand except a 3-nucleotide deletion (AGT) is anneal to the second strand and then extended by the Klenow polymerase to generate the first strand of the adapter.

Figure 3:
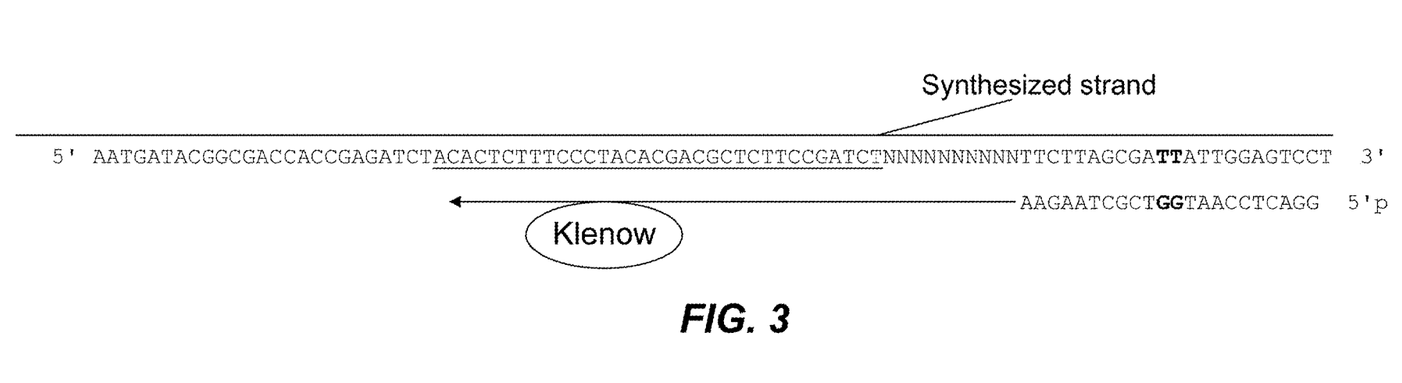
FIG. 3 is a schematic representation of preparing another exemplary substantially complementary double-stranded adapter (SEQ ID NOS: 3 and 12 respectively).

A different approach is shown in FIG. 3. In this embodiment, the first strand is first synthesized to contain a random molecular tag (i.e., NNNNNNNNNN). A primer that is fully complementary to the 3' region of the first strand except lacking an "A" at its 5' terminus and a 2-nucleotide mismatch (i.e., "GG") is annealed to the first strand and then extended by the Klenow polymerase to generate the second strand of the adapter. This approach is more advantageous when adapters with a "T" overhang are needed in ligating with target nucleic acids having an "A" overhang.

A first set of substantially complementary double-stranded adapters may contain at least 16, 32, 48, 64, 100, 128, 200, 500, 1000, 2000, 5000, 10000, 2000, 50000, or 100000 different adapters. In certain embodiments, the first set contains 16-100, 16-1000, 16-5000, 100-1000, 200-2000, 500-5000, 1000-10000, 2000-20000, 10000-1000000, or 20000-2000000 different adapters.

ii. 2$^{nd}$ Adapter

In certain embodiments, a second adapter or a second set of substantially double-stranded adapters may be used in combination with a first set of substantially double-stranded adapters as described above.

(a) 2$^{nd}$ Adapter

The second adapter may be any double-stranded adapter that is able to be linked to target nucleic acids. Preferably, neither strand of the adapter is substantially complementary to target nucleic acids, but at least one strand of the second adapter comprises a sequence that may be used to design a primer for amplifying ligation products. In certain embodiments, one strand of the second adapter may comprise a sequencing primer sequence. In such embodiments, sequencing of adapter-linked target nucleic acids may be performed using a sequencing primer having the sequencing primer sequence of the second adapter.

In certain embodiments, one strand of the second adapter may comprise an index sequence that indicates the sample source from which the target nucleic acids are isolated.

(b) 2$^{nd}$ Set of Adapters

In certain embodiments, a second set of substantially complementary double-stranded adapters may also be used in a ligation reaction. The substantially complementary double-stranded adapters of the second set have the same characteristics as the first set of substantially complementary double-stranded adapters as described above. However, the sequences of the adapters in the second set (e.g., the sequence of 5' region of the first strand and the sequence of 3' region of the second strand) are not substantially identical to those of the adapters in the first set so that a ligation product that contains a target nucleic acid, an adapter of the first set at one end of the target nucleic acid, and an adapter of the second set at the other end of the target nucleic acid does not form an intra-molecular hairpin structure between the sequences of the adapters of the first and second sets when the ligation product is used as a template in an amplification reaction.

In certain embodiments, the adapters of the first and second sets both comprise a 3' region in their first strands and a corresponding 5' region in their second strands. The 3' region of the adapters of the first set may or may not be the same as the 3' region of the adapters of the second set.

A second set of substantially complementary double-stranded adapters may contain at least 16, 32, 48, 64, 100, 128, 200, 500, 1000, 2000, 5000, 10000, 2000, 50000, or 100000 different adapters. In certain embodiments, the second set contains 16-100, 16-1000, 16-5000, 100-1000, 200-2000, 500-5000, 1000-10000, 2000-20000, 10000-1000000, or 20000-2000000 different adapters.

b. Template Nucleic Acids

A nucleic acid sample that contains target nucleic acids to be analyzed may be prepared from any samples that contain nucleic acids of interest. Exemplary include, but are not limited to, samples from a human, animal, plant, bacterium, or fungus, including blood, swabs, body fluid, liver, spleen, kidney, lung, intestine, brain, heart, muscle, pancreas, cell cultures, leaves, stems, flowers, roots, as well as lysates, extracts, or materials and fractions obtained from the samples described above, or any cells, microorganisms and viruses that may be present on or in the samples described above, and the like. A nucleic acid sample may also be prepared from processed samples including preserved, fixed and/or stabilized samples, such as formalin fixed and paraffin-embedded (FFPE samples) and other samples that were treated with cross-linking fixatives such as glutaraldehyde.

Nucleic acids may be isolated from a sample of interest to obtain a nucleic acid sample by any method known in the art useful for nucleic acid isolation or purification. In addition, many kits for nucleic acid preparation are commercially available and may be used, including QIAamp DNA mini kit, QIAamp FFPE Tissue kit, and PAXgene DNA kit.

Any nucleic acids of interest may be analyzed according to the method provided herein. Nucleic acids particularly of interest are those known to be involved in diseases or disorders, including those mutations of which are associated with diseases or disorders or sensitivity or resistance to certain treatments. The diseases or disorders may be any diseases or disorders of interest, including but not limited to various types of cancers (e.g., human breast cancer, colon cancer, leukemia, liver cancer, lung cancer, ovarian cancer, prostate cancer, and gastric cancer), inherited disorders, neurological, metabolic, neuromuscular, developmental, cardiovascular, and autoimmune disorders.

Exemplary genes of interest include but are not limited to EGFR, BRAF, KRAS, ERBB2, PDGFRA, TP53, AKT1, ATM, FBXW7, PIK3CA, ALK, NRAS, BAX, TGFBR2, BRAC1, and BRAC2. Additional genes of interest include those disclosed in U.S. Patent Publication No. US 2013/0005613, which is incorporated by reference.

In certain embodiments, isolated nucleic acids are fragmented to generate target nucleic acid fragments, the ends of which may be repaired to generate blunt ends fragment with 5' phosphorylated ends (e.g., using dNTP, T4 DNA polymerase, Klenow large fragment, T4 Polynucleotide Kinase, and ATP). The 3' ends of the resulting fragments may be added with an "A" to generate a 3'-A overhang (e.g., using dATP, Klenow fragment (3'→5' exo$^-$) or Taq polymerase). Target nucleic acids with a 3'-A overhang may be ligated with adapters having a 5'-T overhang.

c. Ligation Reactions

Methods for ligating adapters to blunt-ended nucleic acids are known in the art and may be used in the DNA sequencing method provided herein. Exemplary methods include those described in Sambrook J and Russell D W, editors. (2001) Molecular Cloning: A Laboratory Manual. 3rd ed. Cold Spring Harbor, N.Y. Cold Spring Harbor Laboratory, Qiagen GeneRead™ Library Prep (L) Handbook and U.S. Patent Application Publication Nos. 2010/0197509, 2013/0005613.

Similarly, methods for ligating adapters having a T overhang with modified amplification products having adenines added to their 3' ends are also known in the art (see, e.g., Qiagen GeneRead™ Library Prep (I) Handbook).

In general, ligation reactions are performed in the presence of a DNA ligase (e.g., T4 DNA ligase) in a reaction buffer (e.g., 1× T4 DNA ligase reaction buffer: 50 mM Tris HCl 10 mM MgCl$_2$, 1 mM ATP 10 mM DTT, pH 7.5) at 4° C. to 37° C., such as 12-16° C.

d. Ligation Products

The ligation reaction may be performed in the presence of only a first set of substantially complementary double-stranded adapters. In certain other embodiments, the ligation reaction may be performed in the presence of a first set of substantially complementary double-stranded adapters and a second double stranded adapter. In yet other embodiments, the ligation reaction may be performed in the presence of two different sets (i.e., a first set and a second set) of substantially complementary double-stranded adapters.

i. A First Set of Adapters

In the embodiments where the ligation reaction is performed in the presence of only a first set of substantially complementary double-stranded adapters, some ligation products may be target nucleic acids with adapters linked to only one end of the target nucleic acids, while some other ligation products may be target nucleic acids with adapters linked to both ends of the target nucleic acids.

ii. A First Set of Adapters and a Second Adapter

In certain embodiments, a ligation reaction is performed in the presence of a first set of substantially complementary double-stranded adapter and a second double-stranded adapter. In such embodiments, the ligation reaction may generate the following ligation products: (a) target nucleic acids linked to an adapter of the first set at only one end of the target nucleic acids, (b) target nucleic acids linked to two adapters of the first set at both ends of the target nucleic acids, (c) target nucleic acids linked to the second adapter at only one end of the target nucleic acids, (d) target nucleic acids linked to the second adapter at both ends of the target nucleic acids, and (e) target nucleic acids linked to an adapter of the first set at one end and to the second adapter at the other end.

Preferably, either the adapters of the first set or the second adapter may carry a group (e.g., a biotin group) to facilitate the isolation of ligation products having two different adapters (i.e., ligation products (e) described above). For example, two adapters, "A" (referring to adapters of the first set) and "B" (referring to the second adapter), are ligated to the ends of nucleic acids. Adapter "B" carries a biotin group, which facilitates the purification of homoadapted nucleic acids (A/A or B/B). The biotin labeled sequencing library is captured on streptavidin beads. Nucleic acids containing the biotin labeled B adapter are bound to the streptavidin beads while homozygous, nonbiotinylated A/A adapters are washed away. The immobilized nucleic acids are denatured after which both strands of the B/B adapted nucleic acids remain immobilized by the streptavidin-biotin bond and single-strand template of the A/B nucleic acids are freed, amplified via a limited number of cycles (e.g., 2-6 PCR cycles), and used as templates in further amplification and/or sequencing.

iii. A First Set Adapters and a Second Set of Adapters

In certain embodiments, a ligation reaction is performed in the presence of a first set of substantially complementary double-stranded adapter and a second set of substantially complementary double-stranded adapter. In such embodiments, the ligation reaction may generate the following ligation products: (a) target nucleic acids linked to an adapter of the first set at only one end of the target nucleic acids, (b) target nucleic acids linked to two adapters of the first set at both ends of the target nucleic acids, (c) target nucleic acids linked to an adapter of the second set at only one end of the target nucleic acids, (d) target nucleic acids linked to two adapters of the second set at both ends of the target nucleic acids, and (e) target nucleic acids linked to an adapter of the first set at one end and to an adapter of the second set at the other end.

Preferably, either the adapters of the first set or those of the second adapter may carry a group (e.g., a biotin group) to facilitate the isolation of ligation products having two different adapters (i.e., ligation products (e) described above). The method for isolating ligation products having an adapter of the first set at one end and the second adapter at the other end described above may also be used to isolate ligation products having an adapter of the first set at one end and an adapter of the second set at the other end.

2. Amplification

Step (b) of the method for performing DNA sequencing of the present disclosure is to perform an amplification reaction using the ligation products of step (a) as templates to generate amplification products that comprise one or more locations ("mismatched locations") that do not form complementary base pairs in the first and second strands of the substantially complementary double-stranded adapters.

Step (b) is typically preformed in the presence of a DNA polymerase. Preferably, DNA polymerases used in step (b) are thermostable. Exemplary DNA polymerases include Taq polymerase (from *Thermus aquaticus*), Tfi polymerase (from *Thermus filiformis*), Bst polymerase (from *Bacillus stearothermophilus*), Pfu polymerase (from *Pyrococcus furiosus*), Tth polymerase (from *Thermus thermophilus*), Pow polymerase (from *Pyrococcus woesei*), Tli polymerase (from *Thermococcus litoralis*), Ultima polymerase (from *Thermotoga maritima*), KOD polymerase (from *Thermococcus kodakaraensis*), Pol I and II polymerases (from *Pyrococcus abyssi*) and Pab (from *Pyrococcus abyssi*), Amplitaq Gold® DNA polymerase (Applied Biosciences), Stoffel fragment of Amplitaq® DNA Polymerase (Roche), KOD polymerase (EMD Biosciences), KOD Hot Start polymerase (EMD Biosciences), Deep Vent™ DNA polymerase (New England Biolabs), Phusion polymerase (New England Biolabs), Klentaq1 polymerase (DNA Polymerase Technology, Inc), Klentaq Long Accuracy polymerase (DNA Polymerase Technology, Inc), Omni KlenTaq™ DNA polymerase (DNA Polymerase Technology, Inc), Omni KlenTaq™ LA DNA polymerase (DNA Polymerase Technology, Inc), Platinum® Taq DNA Polymerase (Invitrogen), Hemo Klentag™ (New England Biolabs), Platinum® Taq DNA Polymerase High Fidelity (Invitrogen), Platinum® Pfx (Invitrogen), Accuprime™ Pfx (Invitrogen), and Accuprime™ Taq DNA Polymerase High Fidelity (Invitrogen).

Step (b) may be performed in the presence of a target-specific primer. Alternatively, this step may be performed in the absence of any target-specific primers.

a. Single Primer Enrichment

In certain embodiments, step (b) is performed in the presence of one or more target-specific primers to enrich target nucleic acids in the amplification products. Because for a given target nucleic acid, only one target-specific primer (as opposed to two target-specific primers that anneal to both strands of a target nucleic acid) is used, this type of amplification is referred to as "single primer enrichment."

A "primer" is an oligonucleotide that is complementary to a target nucleic acid and leads to addition of nucleotides to the 3' end of the primer in the presence of a DNA polymerase using the target nucleic acid as a template.

An "oligonucleotide" refers to a short polymer composed of deoxyribonucleotides, ribonucleotides or combinations thereof. Oligonucleotides are generally between about 10 to about 100 nucleotides, preferably about 12 to about 60 nucleotides, in length.

A target-specific primer comprises a target-specific sequence at its 3' region that specifically binds to a target nucleic acid, which allows the extension of the primer using the target nucleic acid as the template. The target-specific sequence is at least substantially and preferably completely complementary to a region of the target nucleic acid.

In addition to a target-specific sequence at its 3' region, a target-specific primer comprises a 5' region that has one or more additional sequences. For example, the primer may comprise a universal sequence that may be used as a portion of another primer for further PCR amplification, an index sequence that indicates the sample source from which the target nucleic acids are isolated, and/or a sequencing primer sequence.

In the embodiments where multiple different target-specific primers are used for amplifying multiple different target nucleic acids, different target-specific primers comprise the same 5' region, but different target-specific sequences.

In certain embodiments, at least 10, 50, 100, 500, 1000, or 5000, different target-specific primers were included in an amplification reaction according to step (b) of the method disclosed herein. For example, the number of different target-specific primers may be from 10 to 50, 50 to 100, 100 to 500, 500 to 1000, 1000 to 5000, 5000 to 10000, 100 to 1000, 1000 to 10000, or 5000 to 50000.

In certain embodiments, the different target-specific primers target (i.e., are capable of specifically bind to) at least 1, 10, 50, 100, 150 or 200 different genes. For example, the number of different genes targeted by the different primers may be from 1 to 10, 5 to 50, 10 to 100, 50 to 150, 100 to 200 or 150 to 500.

In addition to the target-specific primer(s), the amplification of the ligation products is performed in the presence of another primer referred to herein as an "amplification primer." The amplification primer comprises a portion, or the complete sequence, of the sequence in the 5' region of the first strand of the first set of adapters that is completely complementary to the corresponding sequence in the 3' region of the second strand of the adapters so that the amplification primer is capable of annealing to the second strand of the adapters linked to target nucleic acids and generating amplification products that comprise one or more locations where mismatch(es) occur between the two strands of the adapters. The mismatches are subsequently used to distinguish the two strands of a target nucleic acid, while the molecular tag sequences are used for associating two strands originated from the same target nucleic acid.

Figure 4:
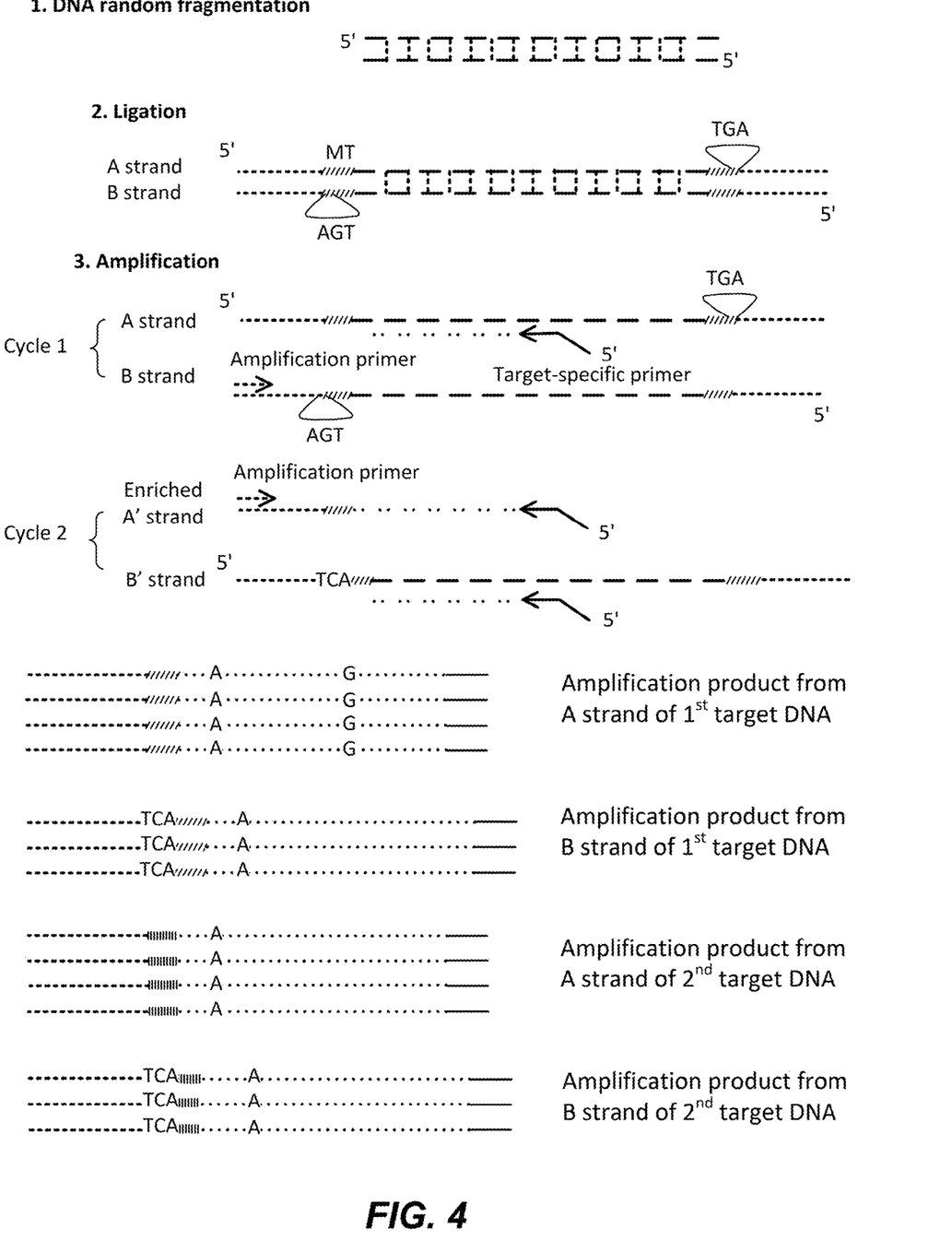
FIG. 4 is a schematic representation of an exemplary single primer enrichment method for single end duplex DNA sequencing method using single primer enrichment.

A schematic representation of the single primer enrichment is FIG. 4. In this figure, step 1 is DNA random fragmentation (which may be accomplished, for example, via mechanical shearing, chemical or enzymatic fragmentation). Step 2 is ligation of substantially complementary double-stranded adapters to a target nucleic acid. The adapters comprise an "AGT" insertion in their second strands. The ligation product shown in FIG. 4 is a target nucleic acid with two adapters linked at its ends. The two adapters are likely to have two different molecular tag sequences. As described above, ligation products may also have an adapter only linked to one end of target nucleic acids.

Step 3 is amplification and enrichment of target nucleic acids in the presence of an amplification primer and target-specific primers. The amplification primer has a sequence identical to a sequence at or near the 5' terminus of the 5' region of the first strand of the adapters (which is in "A strand" of the ligation product). The target-specific primer has a sequence at its 3' terminus that is substantially or completely complementary to a region in A strand of the ligation product and an additional sequence at its 5' terminus.

During the first amplification cycle, the target-specific primer is extended using A strand as the template to generate A' strand, and the amplification primer is also extended using B strand as the template to generate B' strand. Because the "AGT" insertion is located in B strand 5' to the location to which the amplification primer anneals, its complement (i.e., "TCA") is incorporated into the B' strand by extension of the amplification primer in the first cycle.

After a few cycles, the amplification products are shown in the bottom portion of FIG. 4. The amplified fragments either contain "TCA" or not. Fragments derived from the same original double-stranded target nucleic acid have the same molecular tags. Within the fragments having the same molecular tags, fragments with "TCA" are derived from one strand while those without "TCA" are derived from the other strand.

Sequencing of the amplification products can be started in one direction from the left side. For example, the 5' region of the first strand of the adapter may comprise a sequencing primer sequence. A sequencing primer having such a sequence may be used in sequencing the amplification product.

Sequencing from the right side is optional for mutation detection and molecular tag correction purposes. For example, the target-specific primer may comprise a second sequencing primer sequence at its 3' terminus.

Mutations have to be present in both strands to be true. In FIG. 4, "A" is an illustration of a true variant, and "G" is an illustration of a false variant. Without the ability of duplex sequencing, "G" may be mistakenly identified as a rare true variant.

In the presence of the amplification primer, it is very unlikely that a ligation product having adapters linked to both ends of a target nucleic acid is used as an amplification template. First, such a ligation product is at a lower percentage than a ligation product with an adapter linked to only one end of a target nucleic acid in a ligation product mixture. Second, the sequence at 5' terminus and the sequence at 3' terminus of such a ligation product are derived from the first and second strands of adapters and are substantially complementary to each other, the two ends of the ligation product form an intra-molecular hairpin, which prevents or interferes with primer annealing to the ligation product.

In certain embodiments, only one amplification step is performed before the amplification products are sequenced. For example, in such embodiments, the 5' region of the first strand of the adapters may contain a sequencing primer sequence, and the amplification primer has a portion or the complete sequence of the sequencing primer sequence or a sequence in the 5' region of the first strand of the adapter located 5' to the sequencing primer sequence. Alternatively, although the 5' region of the first strand of the adapters does not comprise a sequencing primer sequence, the amplification primer has a sequencing primer sequence at or near its 5' terminus. Preferably, the 5' portion of the target-specific primer also contains a universal primer sequence that facilitates subsequent sequencing reactions.

In certain other embodiments, multiple amplification steps are performed before the final amplification products are sequenced. For example, the amplification products of step (b) may be further amplified in the presence of a first universal adapter primer and a second universal adapter primer. The first universal adapter primer may comprise, from 5' to 3', a first sequencing primer sequence, an optional first index sequence and the sequence of the amplification primer or a sufficient portion thereof so that the first universal adapter may anneal to one strand of the amplification products of step (b). The second universal adapter primer may comprise, from 5' to 3', an optional second sequencing primer sequence, an optional second index sequence, and the sequence of the 5' region of the target-specific primer or a sufficient portion thereof so that the second universal adapter primer may anneal to the other strand of the amplification products of step (b). The optional first index sequence of the first universal adapter primer or the optional second index sequence of the second universal adapter primer may be used to indicate the sample source from which the target nucleic acids are isolated. When present, the second sequencing primer sequence in the second universal adapter primer is different from the first sequencing primer sequence in the first universal adapter primer so that a primer comprising the first sequencing primer sequence is able to sequence a target nucleic acid from one end and a primer comprising the second sequencing primer sequence is able to sequence the target nucleic acid from the other end. The resulting amplification products may be even further amplified or directly subject to sequencing analysis.

b. No Target-Specific Primers

In certain embodiments, step (b) is performed in the absence of any target-specific primers. In such embodiments, the templates are ligation products that comprise two different adapters at the two ends of target nucleic acids. Such ligation products may be generated using a second double-stranded adapter or a second set of substantially complementary double-stranded adapters and subsequently isolated as described above.

To amplify a ligation product that comprises an adapter ("Adapter A") of a first set of substantially complementary double-stranded nucleic acids ligated to one end of a target nucleic acid and a second adapter ("Adapter C") ligated to the other end of the target nucleic acid, a primer pair may be used. One primer comprises at its 3' region, a sequence ("Sequence S") in the 5' region of the first strand of Adapter A, while the other primer comprises at its 3' region, a sequence that is identical to a portion of one strand of Adapter C. Sequence S in the 5' region of the first strand of Adapter A is located 5' to the mismatched location(s) so that the amplification product comprises nucleotide(s) at such location(s).

Similarly, to amplify a ligation product that comprises an adapter ("Adapter A") of a first set of substantially complementary double-stranded nucleic acids ligated to one end of a target nucleic acid and another adapter ("Adapter B") ligated to the other end of the target nucleic acid, two primers may be used. One primer comprises at its 3' region, a sequence ("Sequence S") in the 5' region of the first strand of Adapter A, while the other primer comprises at its 3' region, a sequence ("Sequence W") in the 5' region of the first strand of Adapter B. Sequence S in the 5' region of the first strand of Adapter A is located 5' to a mismatched location (i.e., the location where a mismatch between the first and second strands of Adapter A occurs) so that the amplification product comprises a nucleotide at that location. Alternatively, Sequence W in the 5' region of the first strand of Adapter B is located 5' to a mismatched location (i.e., the location where a mismatch between the first and second strands of Adapter B occurs) so that the amplification product comprises a nucleotide at that location. In yet other embodiments, the sequences (i.e., Sequences S and W) in the 5' regions of the first strands of both Adapter A and Adapter B are located 5' to a mismatched location in the respective adapters so that the amplification product comprises nucleotides at both mismatched locations (i.e., the mismatched location in Adapter A and mismatched location in Adapter B).

Figure 5:
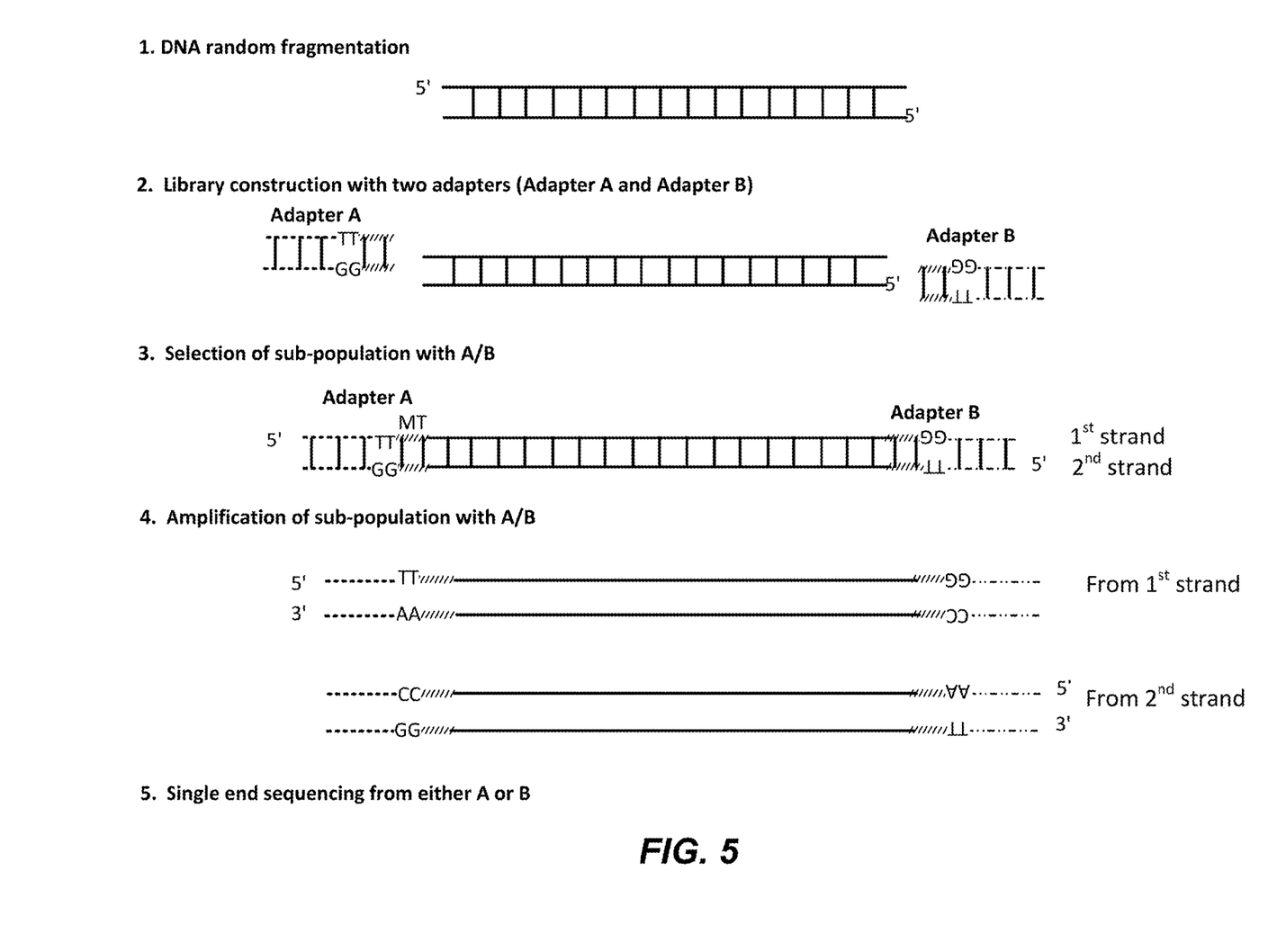
FIG. 5 is a schematic representation of an exemplary single end duplex DNA sequencing method using two sets of substantially complementary double-stranded adapters.

An exemplary method is shown in FIG. 5. First, target nucleic acids are randomly fragmented (see step 1). The resulting target nucleic acid fragments are ligated to two sets of substantially complementary double-stranded adapters (see step 2). Ligation products having primers from two different sets are isolated (see step 3). An example of such ligation products has a target nucleic acid fragment linked to Adapter A at the left end and Adapter B at the right end. There are "TT" mismatches in their 5' regions of the first strands of both Adapter A and Adapter B. Two primers may be used to amplify the ligation product selected in step 3 (see step 4): One primer comprises a sequence of the 5' region of the upper strand of Adapter A located 5' to the "TT" in the upper strand, the other primer comprises a sequence of the 5' region of the lower strand of Adapter B located 5' to the "TT" in the lower strand. The resulting amplification products may be used in single end sequencing from the left end where adapter A is located or from the right end where adapter B is located.

3. Optional Additional Amplification

The amplification products generated above may be further amplified if needed or directly subject to sequencing analysis. The further amplification may be performed in situ, in emulsion or in solution, including bridge PCR and emulsion PCR.

Bridge PCR amplifies DNA fragments flanked with adapters (see, U.S. Pat. No. 5,641,658). A flat surface coated with two types of primers, corresponding to the adapters. Amplification proceeds in cycles, with one end of each bridge tethered to the surface to form DNA colonies or DNA clusters.

Emulsion PCR isolates individual DNA molecules along with primer-coated beads in aqueous droplets within an oil phase (see, Williams et al., Nature Methods 3:545-50, 2006). A polymerase chain reaction then coats each bead with clonal copies of the DNA molecule.

4. Sequencing

Step (c) of the method provided herein is to perform sequencing reactions using amplification products as generated above as templates to obtain sequence reads that comprise mismatched locations in the first and second strands of the substantially complementary double-stranded adapters where complementary base pairs are not formed.

Any high throughput sequencing platforms known in the art may be used to sequence the sequencing libraries prepared as described herein (see, Myllykangas et al., *Bioinformatics for High Throughput Sequencing*, Rodríguez-Ezpeleta et al. (eds.), Springer Science+Business Media, LLC, 2012, pages 11-25). Exemplary high throughput DNA sequencing systems include, but are not limited to, the GS FLX sequencing system originally developed by 454 Life Sciences and later acquired by Roche (Basel, Switzerland), Genome Analyzer developed by Solexa and later acquired by Illumina Inc. (San Diego, CA) (see, Bentley, Curr Opin Genet Dev 16:545-52, 2006; Bentley et al., Nature 456:53-59, 2008), the SOLiD sequence system by Life Technologies (Foster City, CA) (see, Smith et al., Nucleic Acid Res 38: e142, 2010; Valouev et al., Genome Res 18:1051-63, 2008), CGA developed by Complete Genomics and acquired by BGI (see, Drmanac et al., Science 327:78-81, 2010), PacBio RS sequencing technology developed by Pacific Biosciences (Menlo Park, CA) (see, Eid et al., Science 323: 133-8, 2009), and Ion Torrent developed by Life Technologies Corporation (see, U.S. Patent Application Publication Nos. 2009/0026082; 2010/0137143; and 2010/0282617).

In certain embodiments, step (c) is able to determine the sequences of at least 10, 50, 100, 500, 1000, or 5000 target nucleic acid fragments or portions thereof. For example, the number of target nucleic acid fragments or portions thereof that are sequenced in step (c) may be from 10 to 50, 50 to 100, 100 to 500, 500 to 1000, 1000 to 5000, 5000 to 10000, 100 to 1000, 1000 to 10000, or 5000 to 50000.

In certain embodiments, step (c) is able to determine the sequences of at least 1, 5, 10, 50, 100, 150 or 200 different genes or portions thereof. For example, the number of different genes or portions thereof that are sequenced in step (c) may be from 1 to 10, 5 to 50, 10 to 100, 50 to 150, 100 to 200, or 150 to 500.

The method disclosed herein may further comprise step (d) that identifies one or more genetic variations of interest in one or more target nucleic acids. As described above, true genetic variations are those that are present in both strands of target nucleic acids.

The method of the present disclosure helps removing sequencing artefacts and enables detecting genetic variations (e.g., SNVs) present in a nucleic acid sample at very low fractions. In certain embodiment, at least one genetic variation of interest has an allelic frequency of less than 5% in the nucleic acid sample. In certain other embodiments, at least one genetic variation of interest has an allelic frequency of less than 4%, 3%, 2%, or 1% in the nucleic acid sample. The low fraction mutations include those in heterogeneous samples, such as cancer samples.

The method disclosed herein may further comprise step (e) that determines the allelic frequency of at least one of genetic variations of interest in target nucleic acids. This step may use any method and software known in the art that allow such a determination based on sequencing data generated as described herein (see e.g., Kim et al., BMC Bioinformatics 12:231, 2011, and references disclosed therein).

The method disclosed herein may comprise another additional step of determining the copy number of one or more target nucleic acid(s) in a nucleic acid sample. This step may use any method and software known in the art that allows such a determination based on sequencing data generated as described herein. For example, the copy number may be determined by counting unique molecular tags linked to the target nucleic acid(s).

In certain embodiments, the sensitivity of detecting at least one of the genetic variations of interest is at least about 60%, such as at least about 65%, 70%, 75%, 80%, or 85%. Sensitivity is the proportion of actual positives (i.e., the presence of a genetic variation of interest in a target nucleic acid) that are correctly identified as such. It can be expressed as (number of true positions)/(number of true positives+number of false negatives). Preferably, the sensitivity of detecting substantially all (i.e., at least about 75%, such as at least about 80% or 90%) of the genetic variations of interest is at least about 60%, such as at least about 65%, 70%, 75%, 80%, or 85%.

In certain embodiments, the specificity of detecting at least one of the genetic variations of interest is at least about 60%, such as at least about 65%, 70%, 75%, 80%, or 85%. Specificity is the proportion of negatives (i.e., the absence of a genetic variation of interest in a target nucleic acid) that are correctly identified as such. It can be expressed as (number of true negatives)/(number of true negatives+number of false positives). Preferably, the specificity of detecting substantially all (i.e., at least about 75%, such as at least about 80% or 90%) of the genetic variations of interest is at least about 60%, such as at least about 65%, 70%, 75%, 80%, or 85%.

In certain embodiments, both the sensitivity and specificity of detecting at least one of the genetic variations of interest is at least about 60%, such as at least about 65%, 70%, 75%, 80%, or 85%. Preferably, both the sensitivity and specificity of detecting substantially all (i.e., at least about 75%, such as at least about 80% or 90%) of the genetic variations of interest is at least about 60%, such as at least about 65%, 70%, 75%, 80%, or 85%.

As described above, in certain embodiments, molecules subject to sequencing analysis may contain two different sequencing primer sequences at their two ends. In such embodiments, sequencing reactions may be performed from one end using a sequencing primer having either of the sequencing primer sequences or from both ends. Thus, although the present disclosure focuses more on single-end duplex DNA sequencing, it does not exclude certain embodiments where the substantially complementary double-stranded adapters as disclosed herein are used, but sequencing is performed from both ends.

Kits

In another aspect, the present disclosure also provides kits for performing the methods described herein. The kits comprise one or more sets of substantially complementary double-stranded adapters as described above and a ligase in separate containers.

The kits may further comprise one or more of the following components:
 (a) a ligase buffer,
 (b) an amplification primer that comprises a sequence of the 5' region of the first strand of a first set of substantially double-stranded adapters as described above,
 (c) one or more target-specific primers as described above,
 (d) a DNA polymerase as described above, and
 (e) a PCR reaction buffer.

Ligase buffers are known in the art. They typically include a buffering substance to maintain pH (e.g., Tris HCl), a divalent cation (e.g., $Mg^{2+}$), a reducing agent (e.g., DTT), and ATP. Additional components that may be included in a ligase buffer include polyethylene glycol (e.g., PEG 6000 or PEG 8000). An exemplary ligase buffer is 50 mM Tris HCl, 10 mM $MgCl_2$, 1 mM ATP 10 mM DTT, pH 7.5). Another example is 66 mM Tris HCl, pH 7.6, 10 mM $MgCl_2$, 1 mM ATP 10 mM DTT, 7.5% PEG 6000 or PEG 8000.

PCR reaction buffers are known in the art. They typically include a monovalent cation (e.g., $K^+$), a buffering substance to maintain pH (e.g., Tris-HCl), and a divalent cation (e.g., $Mg^{2+}$ and $Mn^{2+}$). Additional components that may be included in PCR reaction mixtures include, for example, one or more of the following components: dimethyl sulfoxide (DMSO), bovine serum albumin (BSA), glycerol, formamide, dimethysulfoxide, tetramethylammonium chloride, potassium glutamate, ammonium sulfate, nonionic detergents, and cationic detergents.

Use

In a related aspect, the present disclosure also provides use of the kits provided herein for performing DNA sequencing, especially single end duplex DNA sequencing and optional downstream analysis.

The methods and kits provided herein are useful in many applications where next generation sequencing is used, including identifying or screening genetic mutations involved in diseases (e.g., tumors and cancer) and genetic pathogen diversity analysis. In addition, next generation sequencing has been used in a variety of fields including metagenomics, paleogenomics, forensics, and human genetics to analyze subpopulations in complex biological samples. Clinical applications include prenatal screening for fetal aneuploidy, early detection of cancer, monitoring patients' response to therapy, and predicting treatment efficacy in individual patients.

The following example is for illustration and not limiting.

Example 1

Single End Duplex Sequencing Via Single Primer Enrichment of Target DNA

Fragmenting gDNA (Sonication Method)

1 ug genomic DNA (gDNA) was diluted in 100 ul elution buffer and sonicated on BIORUPTOR300 (power level low, 10 cycles of 30 seconds on and 30 seconds off). The resulting DNA fragments were purified using QIAGEN's MinElute Column.

Adapter Preparation

The following two oligos were annealed together by heating to 95° C. in 15 ul 1×NEB Buffer 2 and 0.5 mM dNTP for 10 minutes and gradually cooling down to 25° C. (by decreasing the temperature 5° C. every 5 minutes). Then 5 uL of 0.4 U/Klenow Large Fragment Enzyme were added and incubated at 25° C. for 15 minutes. Extended adapter duplexes were purified using Qiagen MinElute PCR Purification Kit.

```
oligo 1:
                                           (SEQ ID NO: 5)
5' AATGATACGGCGACCACCGAGATCTACACTCTTTCCCTACACGACGC

TCTTCCGATCTNNNNNNNNNNNNNNTTCTGAGCGATTATAGGAGTCC*T3' oligo 2:
                                           (SEQ ID NO: 6)
/5phos/GGACTCCTATGGTCGCTCAGAA
```

The underlined sequence in oligo 1 is the sequence of Illumina sequencing primer.
The mismatches in oligo 1 and oligo 2 are indicated in bold and italics.

Library Construction

A sequencing library was prepared using the above-generated gDNA fragments according to the End Repair, A-Addition, duplex Adapter Ligation protocols as described in QIAGEN GeneRead Library Prep for Illumina Kit. The ligation products were purified by 2 rounds Ampure beads purification (0.9× beads ratio). The library was quantified and diluted to 20 ng/ul.

Primer Enrichment

The primer extension reactions were set up as follows:

| Primer Extension | Volume (ul) | |
|---|---|---|
| GeneRead V2 buffer (5x) | 8 | |
| dNTP (2 mM each) | 4 | |
| DNA library (from previous step, 20 ng/ul) | 1 | |
| Taq | 1.6 | |
| Primer pool (76 nM) | 10.5 | 20 nM final |

| Primer Extension | Volume (ul) |
|---|---|
| Ilumina_F primer (10 uM) | 1.6 |
| H$_2$O | 13.3 |
| Total | 40 |

The primer pool contains 445 gene specific primers targeting different gene exons.

```
The 5' sequence common to the 445 gene specific
primers (for primer enrichment):
                                           (SEQ ID NO: 7)
5' AATGTACAGTATTGCGTTTTG 3'

The Illimuna_F primer sequence:
                                           (SEQ ID NO: 8)
5' AATGATACGGCGACCACCGA 3'
```

Primer extension reactions were performed in a thermal cycler as follows: 95° C. for 15 minutes, 8 cycles of 95° C. for 15 seconds and 65° C. for 10 minutes, 72° C. for 5 minutes, and 4° C. hold.

60 ul H$_2$O was added to each of the primer extension mixtures to bring the volume to 100 ul. The extension products were purified by 1 round Ampure beads purification (0.9× beads ratio) and eluted in 15 ul Buffer EB.

Universal PCR

Primer extension products were further amplified in a universal PCR reaction as follows:

| Universal qPCR | Volume (ul) |
|---|---|
| GeneRead V2 buffer (5x) | 5 |
| dNTP (2 mM each) | 2.5 |
| Template (from previous step) | 11.5 |
| Taq | 1 |
| Universal primer (IL2) (4 uM) | 2.5 |
| IL1_ID(#)-RS2 primer (4 uM) | 2.5 |
| Total | 25 |

```
Universal primer (IL2) (for universal PCR):
                                           (SEQ ID NO: 9)
5'AATGATACGGCGACCACCGAGATCTACACTCTTTCCCTACACGACGCT

CTTCCGATCT3'

IL1 ID(#)-RS2 primer (for universal PCR):
                                          (SEQ ID NO: 10)
5'CAAGCAGAAGACGGCATACGAGAT(index)GTGACTGGAGTTCAGAC

GTGTGCTCTTCCGATCTAATGTACAGTATTGCGTTTTG3'
```

The reaction was performed in a thermal cycler as follows: 95° C. for 15 minutes, 26 cycles of 95° C. for 15 seconds and 65° C. for 2 minutes, and 4° C. hold.

The amplification products were purified via one round Ampure beads purification (0.9× beads ratio) and eluted in 20 ul buffer EB. 5 ul of the purified amplification products were checked with a 1.2% Agarose gel.

Library Quantification and Sequencing

Quantification of the amplified library and sequencing were performed according to the manufacturer's instructions.

Results

The sequencing reads from R1 were processed to identify the random barcode region and the presence of either "TT" or "CC" at expected positions. All the reads containing "TT" were derived from original plus strands and all the reads containing "CC" were derived from original minus strand. "TT" read and "CC" read having the same barcode (i.e., molecular tag) were paired to the same double strand DNA molecule. The summary of reads containing "TT" and "CC" is listed in the following table.

| | |
|---|---|
| Total R1 reads | 2,291,759 |
| "TT" reads | 1,537,139 |
| "CC" reads | 479,878 |
| "TT" on-target % | 98.0% |
| "CC" on-target % | 96.6% |
| Total unique barcodes | 171,165 |
| Barcodes associated with "TT" | 128,038 |
| Percent total of barcodes associated with "TT" | 74.8% |
| Barcodes associated with "CC" | 43,127 |
| Percent total of barcodes associated with "CC" | 25.2% |
| Barcodes associated with both "TT" and "CC" (i.e., duplex barcodes) | 23,483 |
| Percent total of barcodes associated with both "TT" and "CC" | 13.7% |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference in their entirety unless contradictory to the disclosure provided herein. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method for determining the sequences of double-stranded target nucleic acids, comprising:
   (a) performing a ligation reaction in the presence of (i) a plurality of double-stranded target nucleic acids comprising target nucleic acid sequences, and (ii) a first set of substantially complementary double-stranded adapters to generate ligation products, wherein
   each adapter of the first set comprises a first strand and a second strand,
   the first strand comprises, from 5' to 3', a 5' region that is 10 or more nucleotides in length and comprises a first sequencing primer sequence, a molecular tag sequence, and an optional 3' region,
   the second strand comprises, from 3' to 5', a 3' region that comprises a sequence fully complementary to a 10-nucleotide or longer portion of the 5' region of the first strand, a fully complementary sequence of the molecular tag sequence of the first strand, and an optional 5' region,
   at least one mismatch between the first and second strands is located in the 3' region of the first strand if the 3' region is present, and/or in the 5' region that is 3' to the 10-nucleotide or longer portion of the 5' region of the first strand, and
   different adapters of the first set comprise different molecular tag sequences in their first strands and corresponding fully complementary sequences of the different molecular tag sequences in their second strands, but are otherwise identical to each other,
   (b) performing an amplification reaction using the ligation products of step (a) as templates to generate amplification products, wherein
   the amplification reaction is performed in the presence of an amplification primer and target-specific primers,
   the amplification primer comprises a sequence of the 5' region of the first strand of the double-stranded adapters of step (a),
   the target-specific primers each comprise, from 5' to 3', a 5' region and a target-specific sequence that is complementary to a region of the target nucleic acid sequence in the strand of one of the target nucleic acids that links to the first strand of the adapter, different target-specific primers comprising the same 5' region but different target-specific sequences, and the amplification products comprise one or more locations that do not form complementary base pairs in the first and second strands of the substantially complementary double-stranded adapters, (c) performing sequencing reactions using amplification products of step (b) or their further amplification products as templates and a sequencing primer that comprises the sequencing primer sequence introduced in the first strand of the substantially complementary double-stranded adapters of step (a) to obtain sequencing reads that comprise the one or more locations where a complementary base pair is not formed in the first and second strands of the double-stranded adapters, and (d) determining the sequence of each double-stranded target nucleic acid based on the sequencing reads from only one end of the double-stranded target nucleic acid.

2. The method of claim 1, further comprising, between steps (b) and (c):

(x) amplifying the amplification products of step (b) in the presence of a first universal adapter primer and a second universal adapter primer, wherein the first universal adapter primer comprises, from 5' to 3', the first sequencing primer sequence, and the sequence of the amplification primer or a sufficient portion thereof, and the second universal adapter primer comprises, from 5' to 3', an optional second sequencing primer sequence, an optional second index sequence, and the sequence of the 5' region of the target-specific primer or a sufficient portion thereof.

3. The method of claim 1, wherein the ligation reaction in step (a) is performed in the presence of a second set of substantially complementary double-stranded adapters, wherein each adapter of the second set comprises a first strand and a second strand, the first strand comprises, from 5' to 3', a 5' region that is 10 or more nucleotides in length, a molecular tag sequence, and an optional 3' region, the second strand comprises, from 3' to 5', a 3' region that comprises a sequence fully complementary to a 10-nucleotide or longer portion of the 5' region of the first strand, a fully complementary sequence of the molecular tag sequence of the first strand, and an optional 5' region, at least one mismatch between the first and second strands is located in the 3' region of the first strand if the 3' region is present, and/or in the 5' region that is 3' to the 10-nucleotide or longer portion of the 5' region of the first strand, and different adapters of the second set comprise different molecular tag sequences in their first strands and corresponding fully complementary sequences of the different molecular tag sequences in their second strands, but are otherwise identical to each other, and the 5' region of the first strand of the second set is not substantially complementary to the 3' region of the second strand of the first set.

4. The method of claim 1, further comprising (e) identifying one or more genetic variations of interest in one or more of the target nucleic acid sequences.

5. The method of claim 4, wherein at least one of the genetic variations has an allelic frequency of 5% or less in a nucleic acid sample that comprise the target nucleic acids.

6. The method of claim 4, further comprising (f) identifying (e) determining the allelic frequency of at least one of the genetic variations of interest in one or more target nucleic acid sequences.

7. The method of claim 1, wherein the molecular tag sequences in the first set of substantially complementary double-stranded adapters are completely defined.

8. The method of claim 1, wherein the molecular tag sequences in the first set of substantially complementary double-stranded adapters are completely random or semi-random.

9. The method of claim 1, wherein the molecular tag sequences in the first set of substantially complementary double-stranded adapters are 2 to 15 nucleotides in length.

10. The method of claim 1, wherein the 5' region in the first strand of the double-stranded adapters is 10 to 75 nucleotides in length.

11. The method of claim 1, wherein at least one mismatch between the first and second strands of the double-stranded adapters is located in the 5' region of the first strand of the adapters.

12. The method of claim 1, wherein the first strand of double-stranded adapters comprises a 3' region.

13. The method of claim 12, wherein the 3' region is 2 to 30 nucleotides in length.

14. The method of claim 12, wherein the 3' region comprises one or more mismatches between the first and second strands.

15. The method of claim 1, wherein the number of mismatches between the first and second strands of the double-stranded adapters is 1 to 6.

16. The method of claim 1, wherein the set of the substantially complementary double-stranded adapters comprises at least 16 different adapters.

* * * * *

UNITED STATES PATENT AND TRADEMARK OFFICE
CERTIFICATE OF CORRECTION

| | | |
|---|---|---|
| PATENT NO. | : 11,821,028 B2 | Page 1 of 1 |
| APPLICATION NO. | : 16/316832 | |
| DATED | : November 21, 2023 | |
| INVENTOR(S) | : Yexun Wang | |

It is certified that error appears in the above-identified patent and that said Letters Patent is hereby corrected as shown below:

In the Claims

Column 28, Claim 6, Line 18:
"(e) determining the allelic frequency" should read: --the allelic frequency--.

Signed and Sealed this
Twentieth Day of May, 2025

Coke Morgan Stewart
*Acting Director of the United States Patent and Trademark Office*